United States Patent [19]

Lehtinen et al.

[11] Patent Number: 5,403,829

[45] Date of Patent: Apr. 4, 1995

[54] USE OF BISPHOSPHONATES IN ENDO-OSTEAL BONE SURGERY

[75] Inventors: Risto T. Lehtinen, Paattinen; Markku Nyman, Klaukkaala; Pekka Paavolainen, Helsinki, all of Finland

[73] Assignee: Leiras Oy, Turku, Finland

[21] Appl. No.: 36,140

[22] Filed: Mar. 24, 1993

[51] Int. Cl.$^6$ .............................................. A61K 31/66
[52] U.S. Cl. .................................... 514/102; 514/108
[58] Field of Search .................. 514/102, 108

[56] References Cited

U.S. PATENT DOCUMENTS

| | | | |
|---|---|---|---|
| 4,067,971 | 1/1978 | Francis et al. | 514/108 |
| 4,234,645 | 11/1980 | Gunther et al. | 514/108 |
| 5,227,506 | 7/1993 | Saari et al. | 514/108 |
| 5,270,365 | 12/1993 | Gertz et al. | 514/108 |

OTHER PUBLICATIONS

Lehtinen, R. and A. Raunio, "The Effect of Chlodronate in the Rabbit Tibia Implanted with a Titanium Screw and an Osseointegration in Man". Abstract, Internationales Symposium, Oct. 6–9, 1991, Universität Rostock Medizinische Fakultät Klinik Und Poliklinik Für Mund-Kiefer-Gesichtschirurgie.

*Primary Examiner*—Raymond Henley, III
*Assistant Examiner*—T. J. Criares
*Attorney, Agent, or Firm*—Adduci, Mastriani, Schaumberg & Schill

[57] ABSTRACT

A method of enhancing the formation of bone tissue and/or eliminating late complications subsequent to bone surgery comprising administering an amount, which is safe and sufficient to promote the formation of bone tissue and/or eliminate late complications, of a compound of formula

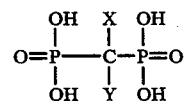

wherein X is H, OH, Cl, F or a methyl group and Y is Cl, OH, $-(CH_2)_2-N(CH_3)-(CH_2)_4-CH_3$, $-(CH_2)_n CH_3$ or $-(CH_2)_n-NH_2$, where n is zero or an integer of 1 to 8, $-NHZ$, where Z is pyridinyl or cycloheptyl, $-SZ'$, where Z' is pyridinyl or chloro-substituted phenyl, or Y is a pyridinylsubstituted lower alkyl chain; or a non-toxic, pharmaceutically acceptable salt or ester thereof to a bone surgery patient.

11 Claims, 13 Drawing Sheets

USE OF BISPHOSPHONATES IN ENDO-OSTEAL BONE SURGERY

BACKGROUND OF THE INVENTION

1. Field of the Invention

This invention relates to the use of a certain group of bisphosphonates for the regeneration of bone tissue and/or elimination of late complications subsequent to bone surgery. More particularly, the invention concerns the use of clodronate to enhance bone tissue formation after surgical replacement of endo-osteal material such as implantations, particularly dental implantations, and transplantations.

2. Description of the Prior Art

Bisphosphonates are synthetic organic compounds structurally related to pyrophosphate in that the pyrophosphate P-O-P-bond is replaced by a P-C-P-bond. In contrast to pyrophosphate, bisphosphonates are resistent to enzymatic hydrolysis in osseous tissue. The bisphosphonates are potent inhibitors of bone resorption and they have been successfully used in the treatment of hypercalcemia caused by various reasons. A great number of bisphosphonates have been studied, but only clodronate, etidronate and pamidronate have reached wider clinical use.

The main effect of the bisphosphonates is their ability to inhibit bone resorption, but contrary to the effect on mineralization, the mechanism involved is cellular (Fleisch H., Drugs 1991; 42: 919–44). These different effects vary greatly according to the structure of the individual bisphosphonate compound. The half-life of circulating bisphosphonates is very short, in the order of minutes to hours. Of a given dose, 20 to 50% is taken up by the skeleton, the rest being excreted in the urine. The half-life in bone is far longer and depends upon the turnover rate of the skeleton itself.

A review (Mian M. et al., Int J Clin Pharmacol Res. 1991; 11: 107–14) of 126 publications on clinical studies concerning the use of clodronate in the therapy of bone disease, involving 1930 patients, in order to evaluate the tolerability and the effects following short- and long-term administration of this drug, indicates that clodronate therapy does not have any clinically significant side-effects and confirm its tolerability and safety.

Of the many compounds belonging to the bisphosphonate family, clodronate has been widely used in hypercalcemia and osteolysis of malignancy (Bonjour J. P. and Rizzoli R., Calcif Tissue Int 1990; 46 Suppl: 20–25). All published reports indicate that clodronate can normalize plasma calcium in the majority of hypercalcemic, rehydrated cancer patients in whom increased bone resorption is the prevailing disturbed calcium flux (Fleisch H., Drugs 1991; 42: 919–44).

Various phosphonate compounds are also reported in the patent literature as being useful in the treatment of anomalous mobilization and deposition of calcium phosphate salts (bone mineral) in mammals. Reference is made to U.S. Pat. Nos. 3,678,164; 3,662,066; 3,553,314; 3,553,315; 3,584,124; 3,584,125 and 3,641,246. U.S. Pat. No. 3,683,080 discloses the use of clodronate and various other phosphonates for the treatment of anomalous calcification involving soft tissues and arthritic conditions. U.S. Pat. No. 4,234,645 discloses clodronate as useful in the treatment of various collagen diseases.

As discussed above, bisphosphonates are well documented with respect to their ability to inhibit bone resorption in connection with various diseases. The use of these compounds to promote bone tissue formation subsequent to surgical operations relating to endo-osteal prosthesis such as hip prostheses, plates used in internal rigid fixation and various kinds of implantations; osteomyelitis after decorticalization of necrotics from the mandible or bone transplantations has, however, never been suggested. Particularly in dental implantation surgery, patients with severe atrophy of the mandibular alveolar process are difficult to treat by conventional implant techniques. At the abutment connection operation mobile fixtures are found frequently. About half of the number of recorded failures occurred under the healing period (Adell R. et al., Int J Oral & Maxillofac Surg 1990, 5: 347–359). Autogenous bone grafts used for severely resorbed ridge augmentation usually resorb to a considerable extent (Baker R. D. et al., J Oral Surg 1970; 37: 486–89).

SUMMARY OF THE INVENTION

It has now been found that bisphosphonates are useful to promote bone formation subsequent to bone surgery and to eliminate late complications due to implantations, particularly hip prostheses. For the purpose of this invention the term "bone surgery" shall be understood to include surgical operations relating to endo-osteal prostheses such as hip prostheses, plates used in internal rigid fixation and various kinds of implantations of artificial implants into the human body such as dental implants; treatment of osteomyelitis after decorticalization of necrotics from the mandible; and bone transplantations. The invention particularly concerns oral surgery, especially the introduction of artificial tooth implants.

DESCRIPTION OF PREFERRED EMBODIMENTS

The present invention relates to a method of enhancing the formation of bone tissue and/or eliminating late complications subsequent to bone surgery comprising administering an amount, which is safe and sufficient to promote the formation of bone tissue and/or eliminate late complications, of a compound of formula (I)

wherein X is H, OH, Cl, F or a methyl group and Y is Cl, OH, —(CH$_2$)$_2$—N(CH$_3$)—(CH$_2$)$_4$—CH$_3$, —(CH$_2$)$_n$—CH$_3$ or —(CH$_2$)$_n$—NH$_2$, where n is zero or an integer of 1 to 8, —NHZ, where Z is pyridinyl or cycloheptyl, —SZ', where Z' is pyridinyl or chloro-substituted phenyl, or Y is a pyridinylsubstituted lower alkyl chain; or a non-toxic, pharmaceutically acceptable salt or ester thereof to a bone surgery patient before and/or after said surgery.

Particularly valuable members of formula (I) for the purpose of this invention are clodronate, where X and Y both are Cl; pamidronate, where X is OH and Y is —(CH$_2$)$_2$—NH$_2$; alendronic acid, where X is OH and Y is —(CH$_2$)$_3$—NH$_2$; neridronic acid, where X is OH and Y is —(CH$_2$)$_5$—NH$_2$; risedronic acid, where X is OH and Y is 3-pyridinylmethyl; tiludronate, where X is H and Y is 4-chlorophenylthio; YM-175 (cycloheptylamino)methylenebisphosphonic acid, where X is H and Y is cycloheptylamino; BM-210995,-1-hydroxy-3-(methylpentylamino)-propylidenebisphosphonic acid, where X is OH and Y is —(CH$_2$)$_2$—N(CH$_3$)—(CH$_2$)$_4$—CH$_3$ and etidronate, where X is methyl and Y is OH. The most preferable compound for the purpose of the invention is clodronate or a pharmaceutically acceptable salt or ester thereof.

The pharmaceutically acceptable salts and esters useful in the practice of this invention can be described by formula (II)

wherein X and Y are as defined above and M is hydrogen, a pharmaceutically acceptable cation, preferably an alkali metal cation such as sodium or potassium, or an alkyl or aryl moiety, e.g. an alkyl group of 1 to 4 carbon atoms or phenyl.

For the purpose of the invention the compounds of formula (I) or their pharmaceutically acceptable salts and esters can be administered by various routes. The suitable administration forms includes systemic use such as oral formulations; parenteral injections including intravenous, intramuscular, intradermal and subcutanous injections; and suppositories. The compounds can also be administered locally by laying on or spreading the compounds or compositions thereof directly on the tissue to be treated.

The required dosage of the compounds of formula (I) or their salts will vary with the particular condition being treated, the severity of the condition, the duration of the treatment, the administration route and the specific bisphosphonate being employed. A single daily dose can range from 0.01 to 100 mg per kilogram body weight. Doses higher than 100/kg/day may produce toxic symptoms and should be avoided. For parenteral administration (s.c; i.p.; i.m.), the preferable bisphosphonate daily doses range from 0.5 to 20 mg/kg. For i.v. administration the most preferable daily doses are 0.5 to 5 mg/kg. For oral administration the preferred daily doses range from 10 to 100 mg/kg. For local treatment a solution of 5 to 100 mg/ml of a bisphosphonate should preferably be used before replacement of endosteal material.

The medication should preferably start 1 to 3 weeks before the surgery to obtain the optimal bisphosphonate concentration in bone. After the surgery, the medication should preferably be continued for a period of 1 to 6 months.

The inventive idea was verified by animal and clinical tests. According to two separate studies with clodronate disodium, the methods and results of which are presented in detail below, the effect of clodronate on bone tissue formation is demonstrated.

In the first test, the effect of clodronate on bone regeneration was tested in rabbit tibia. An experimental model involving free bone transplantation to the tibia was developed. The tests revealed that clodronate had a positive effect on bone regeneration in the donor cavity and in the free bone grafts transplanted using a titanium screw. Clodronate-treated tibiae were more quickly and more extensively vascularized than the control tibiae.

The results of human studies, where the patients had an extra implant that was removed after a certain period of time, demonstrated that clodronate-medicated patients exhibited a more rapid bone formation than the unmedicated control group.

Because of the close structural and pharmacological relationship between clodronate and its analogues as represented by formula (I) above it is justified to believe that the remaining members of formula (I) also are effective to promote the bone tissue formation and to eliminate late complications after surgery.

EXPERIMENTS

I. Effect of Clodronate on Bone Regeneration in Rabbits

The aim of the study was to determine whether clodronate had a positive effect on vascularization and bone formation in the tibia of a rabbit in which bone was transplanted with the aid of a titanium screw.

Materials and methods

Sixteen skeletally mature (3.5–3.9 kg) New Zealand white male rabbits were used. The animals were divided into two groups. Each group consisted of eight animals (16 tibiae). One group received clodronate disodium (Bonefos ®, Leiras Oy, Finland) 25 mg/kg i.m. twice a week. The other group (control) was untreated.

The rabbits were anesthetized with an i.m. injection of 2.8 mg of Ketalar ® (Parke-Davis, Spain) and 2.0 ml of Rompun ® (Bayer, Germany).

Figure 1:
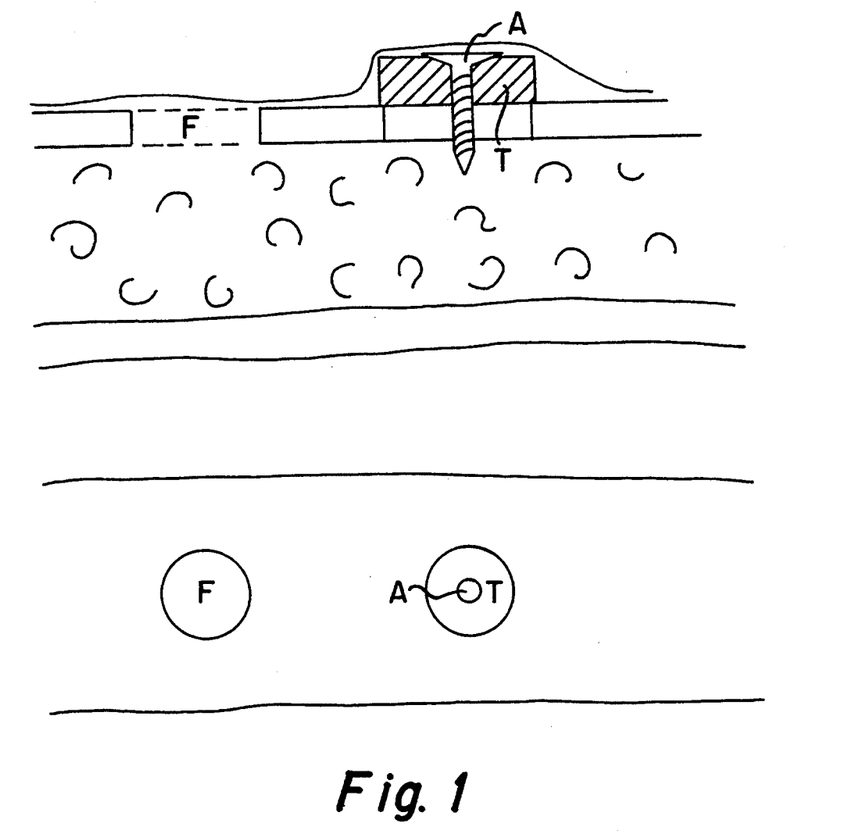
FIG. 1 is a drawing illustrating a cross-section and a top-view of a rabbit tibia showing a bone transplanted with a titanium screw.

The proximal ends of both tibiae were exposed and the periosteum removed from the operative area. A piece of cortical bone 4 mm across was removed using a trepan bur. A 0.6 mm titanium implant screw (Filpin, Filpol Dental, Ireland) was screwed through the piece. The piece, perforated with the implant, was screwed into place 3 mm above the donor cavity. Reference is made to FIG. 1 representing the rabbit tibia, where A means the implant, T the transplant and F the donor cavity. The upper drawing of the Figure represents the cross section and the lower drawing the tibia as seen from above.

Figure 2:
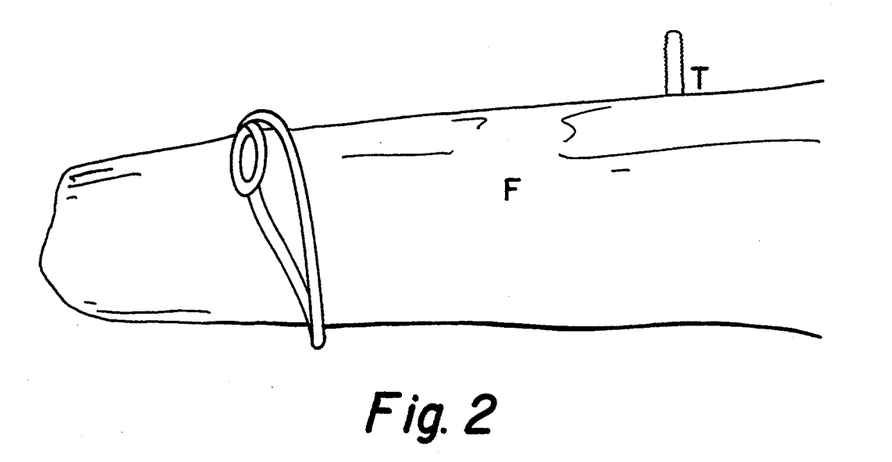
FIG. 2 is a lateral roentgen picture of a rabbit tibia showing a bone transplant as described in Experiment (I).

The animals were divided into two groups: microangiography was performed on eight animals and histological staining specimens was carried out from the other eight animals. Roentgenological examinations with two steel wires with knots twisted around the tibiae to determine the exact positions of implant and donor cavity were performed. Reference is made to FIG. 2, which discloses a lateral roentgen picture of tibia in the operation area. The letters A, T and F have the same meaning as in FIG. 1.

Histological evaluation

Eight animals were killed for histological evaluations at various times after implantation: after 14 days (2 rabbits), 21 days (4 rabbits) and 35 days (2 rabbits). The number of control and clodronate-treated animals was the same each time.

Tibiae were fixed with 5% phosphate-buffered formalin and toluine blue staining and hematoxylin eosin (HE) were carried out. Specimens were inspected under a light microscope and adverse effects or signs of inflammation were recorded.

Microangiography

Eight animals (4 controls, 4 treated) were killed after 21 days by means of an i.v. dose of pentobarbital.

Before death the abdominal artery and vein were exposed and an 18-gauge angiocath was inserted and tied in place. A 20 ml syringe containing heparinized saline was used to infuse the abdominal artery. Infusion continued until a clear venous effluent emerged from the transacted abdominal veins. A 100 ml syringe filled with an orange-colored silicone rubber compound (Micro-Fil ®, Canton Biomedical, Boulder, Colo., USA) was then injected until orange effluent emerged from the abdominal veins. After the compound had set for 4 hours, the tibiae were separated. The specimens were then sequentially dehydrated according to the cleaning technique of the manufacturer.

Using a scalpel, cross-sections were cut through the midportions of the grafts for viewing and slide photography under a dissecting microscope. The absolute number of vessels penetrating the transplant host junction was counted by means of color transparencies (Eppley B. et al., J Oral Maxillofac Surg 1988; 46: 391–98).

The vessel count was performed in the specimen where the most vessels were observed. Vessels were counted on two separate occasions by the same observers and the results were averaged. If the variation between two values was greater than 10%, a third count was undertaken and the three counts were averaged. Vessel counts in both groups were compared using a paired t-test; P values less than 0.05 were considered significant.

Results

The clinical observations revealed that all wounds healed uneventfully.

Evaluation of angiogenesis

When counting the vessels, most of them were clearly visible. It was, however, difficult to count the small vessels in the bone-transplant and bone-donor cavity junctions. Because of the variation in the two values by the same observer the third count was undertaken in five specimens.

Donor cavities

The number of vessels penetrating into the donor cavities was greater in rabbits treated with clodronate than for the control. The results are given in Table I below and the difference is statistically significant ($P<0.05$).

TABLE I

| Number (x) of vessels penetrating donor cavity | | | |
|---|---|---|---|
| | x | S.D. | Number of tibiae |
| Control | 12.3 | 4.6 | 8 |
| Clodronate treated | 26.3 | 4.0 | 8 |

Figure 3:
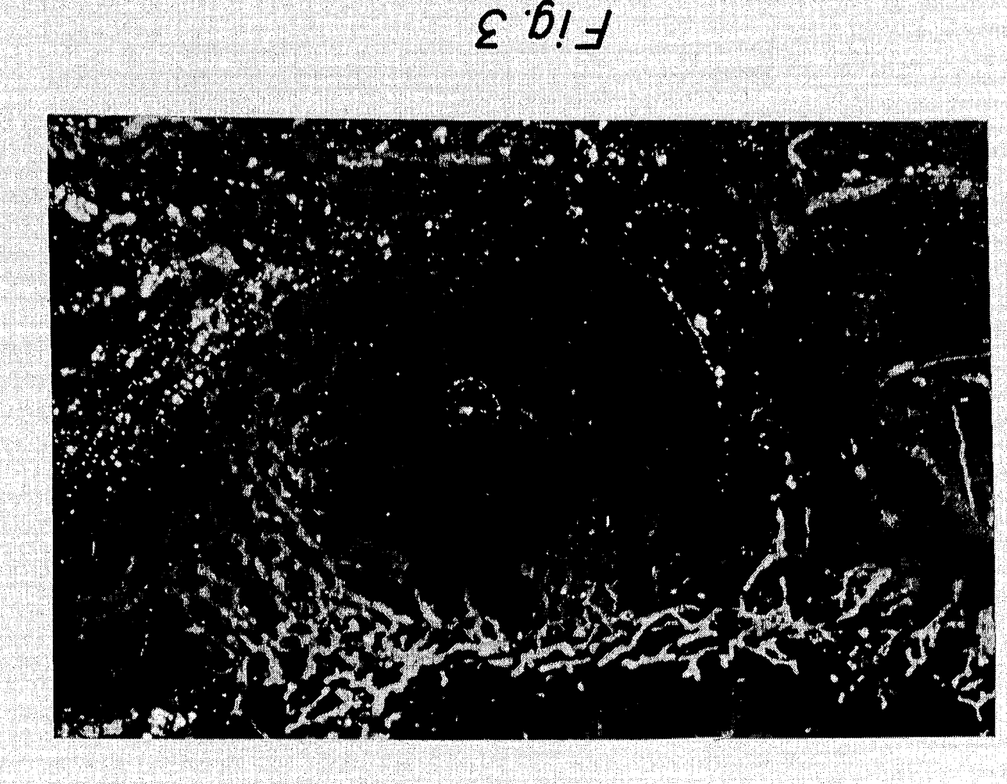
FIG. 3 is a photomicrograph showing a 21-day tibia specimen from a rabbit treated with clodronate used for evaluating angiogenesis as described in Experiment (I).
Figure 4:
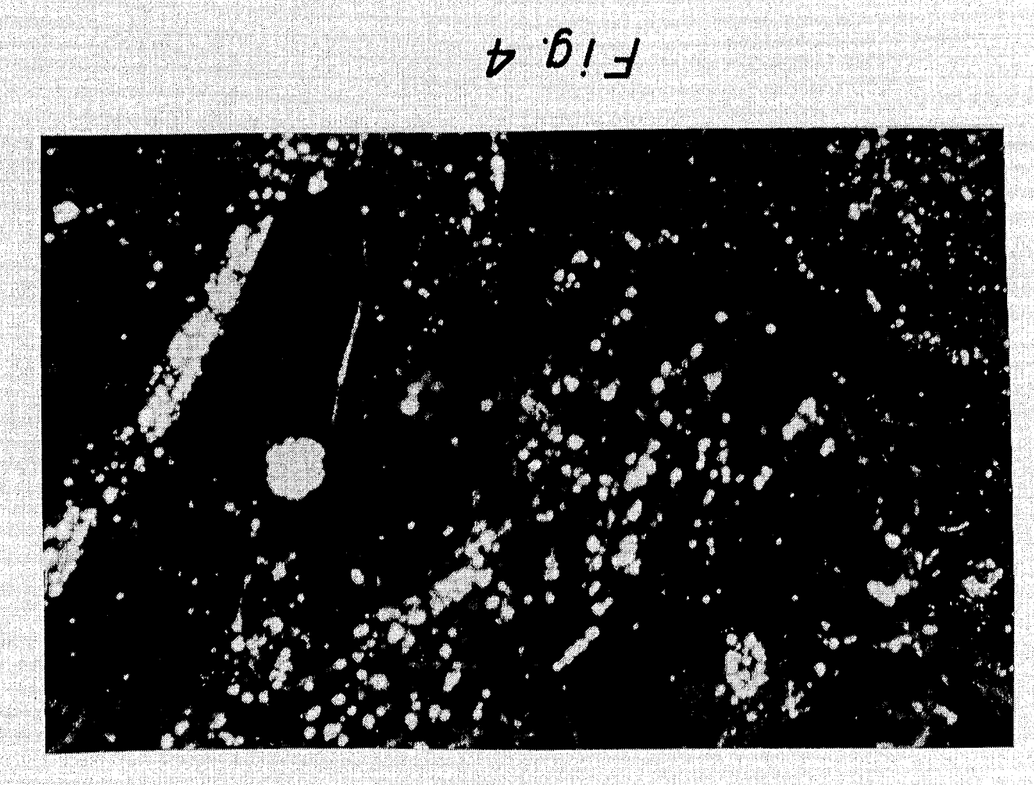
FIG. 4 is a photomicrograph showing a 21-day tibia specimen from an untreated rabbit used for evaluating angiogenesis as described in Experiment (I).

The difference in the amount of vessels can also be observed from the photographs of FIGS. 3 and 4. FIG. 3 discloses a 21-day specimen from a rabbit treated with clodronate. Implant and transplant are located in the centre of the picture. The donor cavity is seen to the right of the transplant. It can be seen that many vessels penetrate the donor cavity and transplant. FIG. 4 shows a 21-day specimen from an untreated rabbit. Only a small number of vessels penetrated the transplant.

Transplants

The transplants in the tibiae from the clodronate-treated animals became vascularized sooner and more extensively than in the tibiae from the control. The difference was statistically significant ($P<0.05$). The results are presented in Table II.

TABLE II

| Number (x) of vessels penetrating transplant | | | |
|---|---|---|---|
| | x | S.D. | Number of tibiae |
| Control | 4.75 | 1.7 | 8 |
| Clodronate treated | 13.0 | 4.0 | 8 |

The vessels penetrated closer to the centre of the cavity in the medicated rabbits than in the control group. In the medicated rabbits the number of vessels from one side of the specimen was greater than from the opposite side.

Histological findings

No signs of adverse tissue reactions or inflammation were observed when the specimens were studied under the light microscope.

Donor cavity

The 14-day control specimens exhibited slight collagen formation and were partly devoid of histologically visible elements in the middle part of the cavity. The clodronate-treated specimens exhibited more collagen formation than the control specimens. No empty spaces were seen. At three weeks, the control specimens exhibited only slight bone formation at the outer edges of the cavity. The inner part of the cavity was mainly filled with collagen and a sharp line between the cavity and bone was clearly seen. The clodronate-treated donor cavities were almost completely filled with new bone. Collagen was still found between new bone in the three-week specimens.

Figure 5:
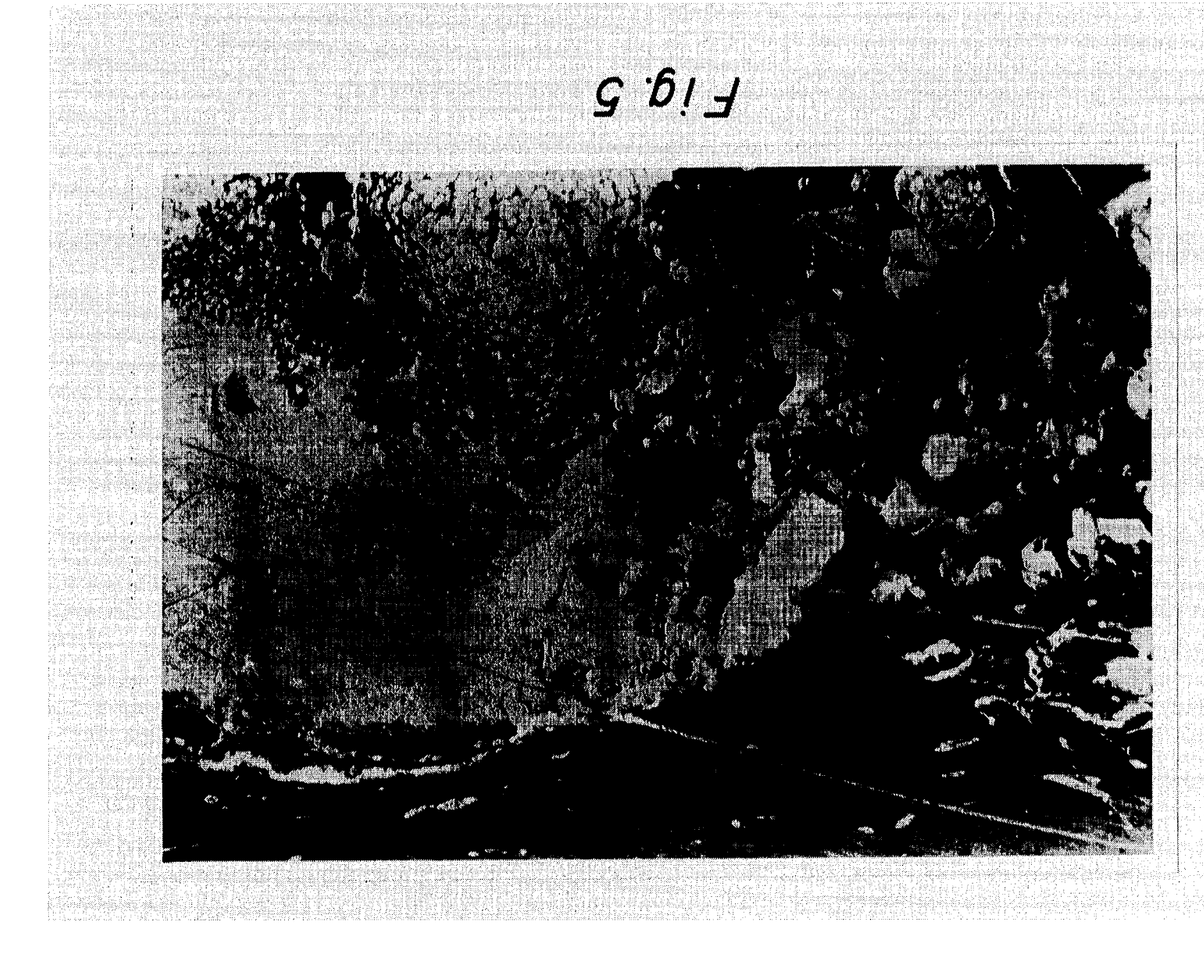
FIG. 5 is a photomicrograph of a five-week control cavity of a rabbit tibia as described in Experiment (I).
Figure 6:
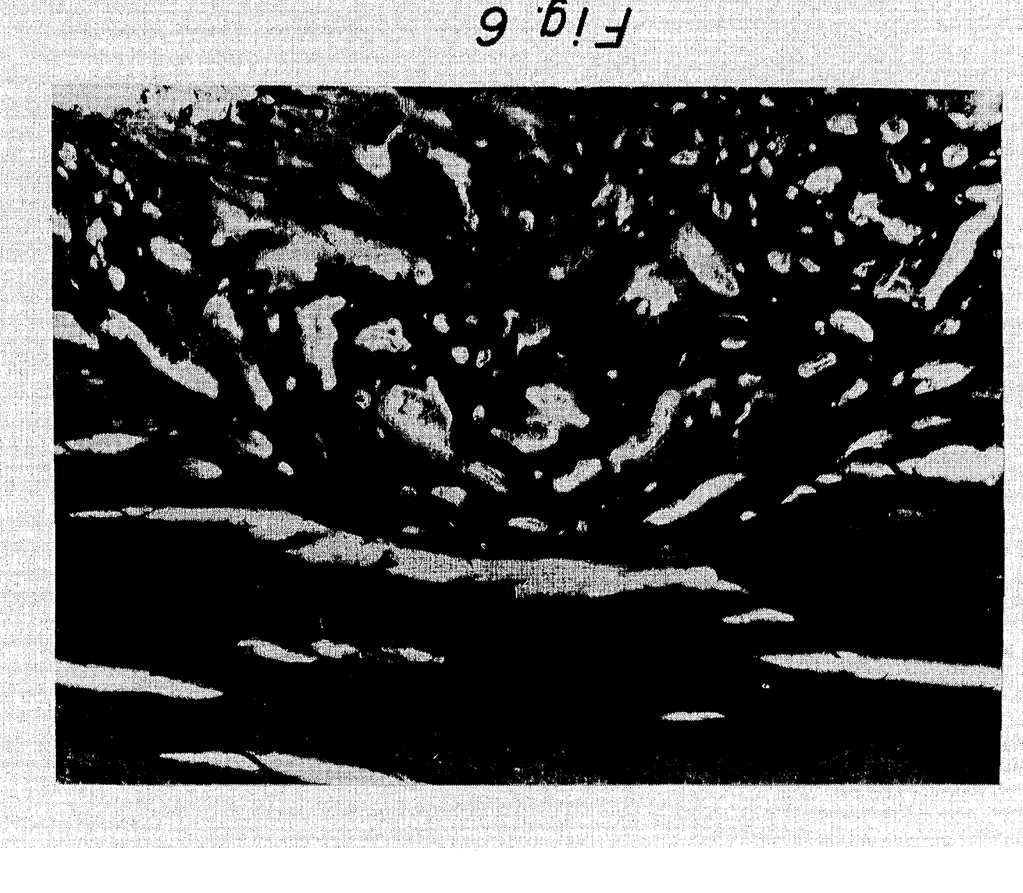
FIG. 6 is a photomicrograph of a five-week clodronate-treated cavity of a rabbit tibia as described in Experiment (I).
Figure 7:
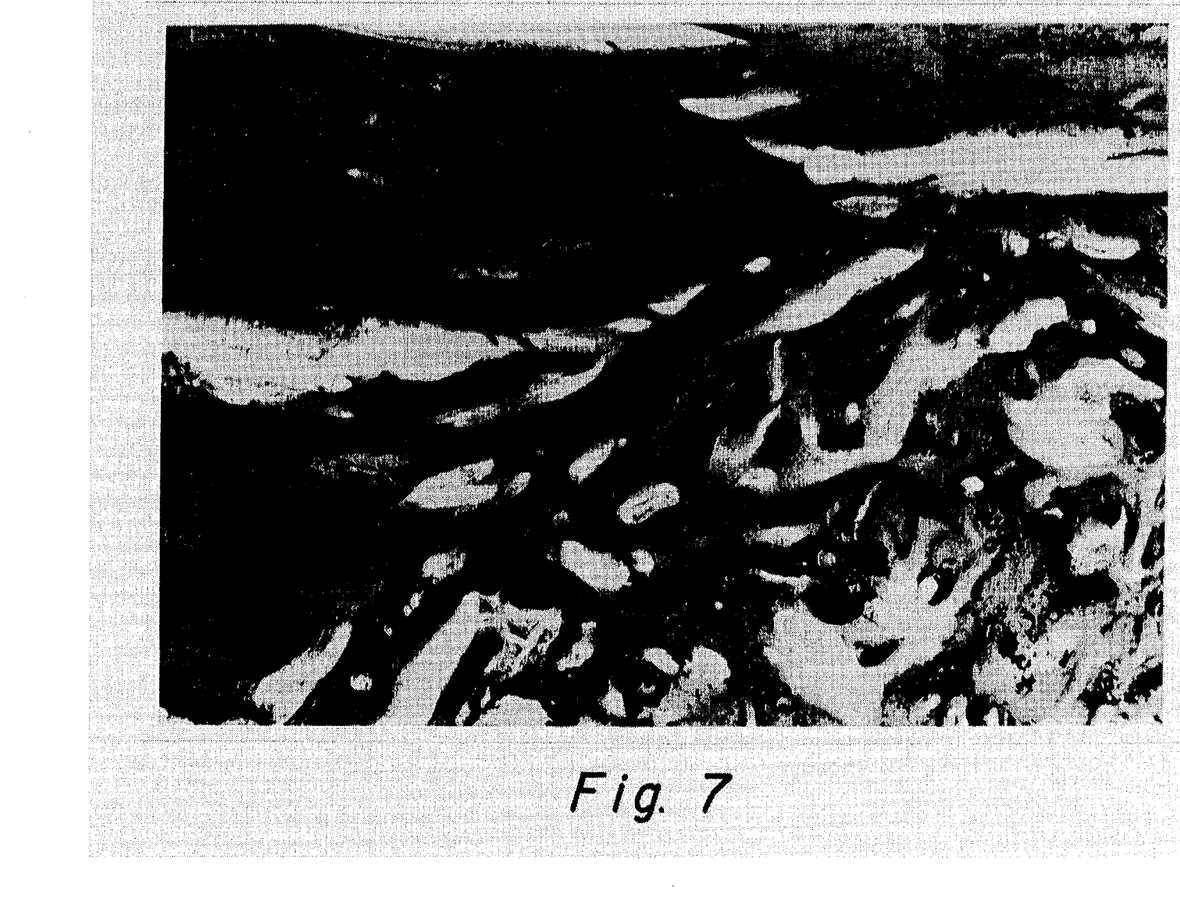
FIGS. 7 and 8 are greater magnified photomicrographs of the clodronate-treated cavity shown in FIG. 6.
Figure 8:
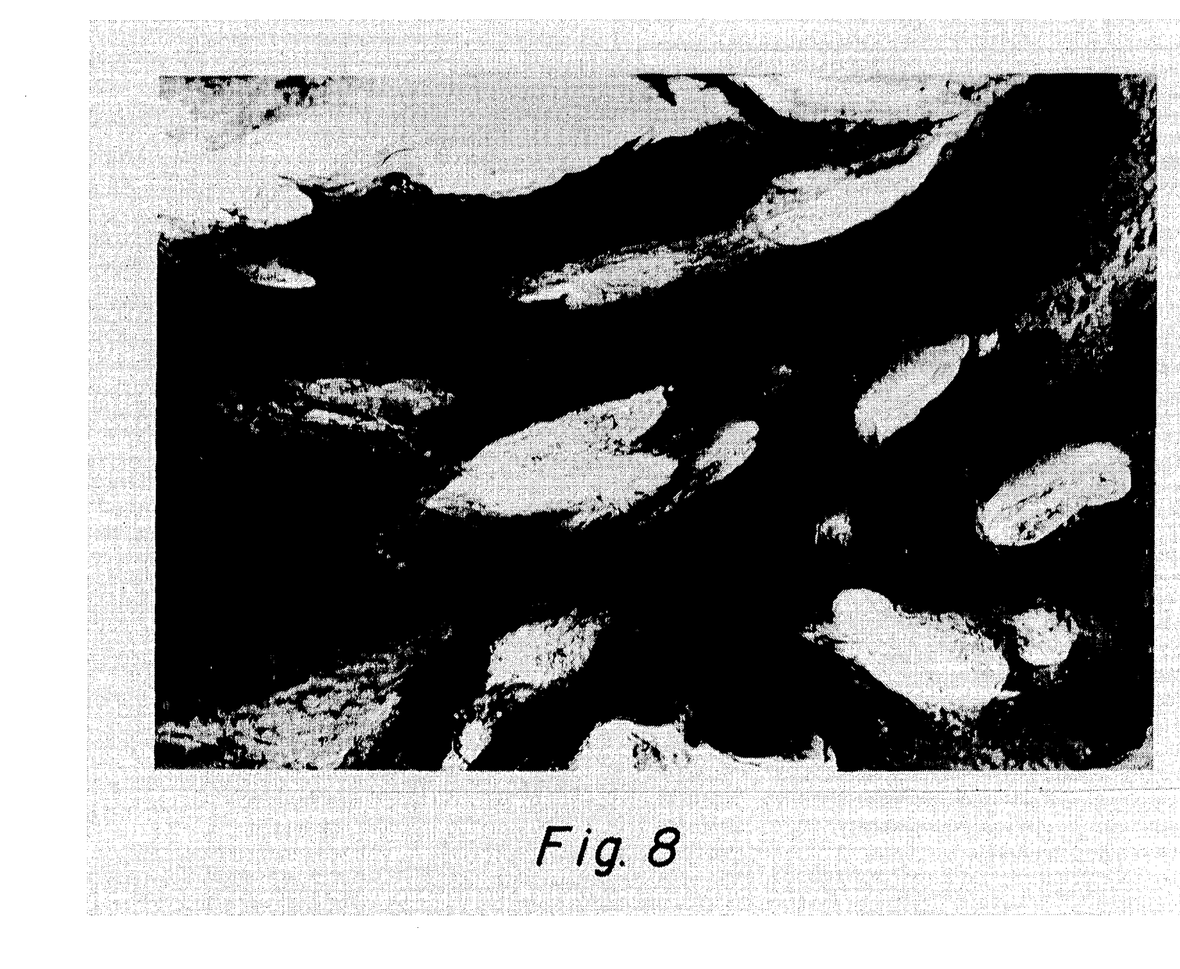

The five-week control cavities were partly filled with new bone, and the line between drilled cavity and bone was still seen in most parts of the cavity. The clodronate-treated cavities were completely filled with new bone and the drilling line was visible but the resolution between the donor cavity and old bone had started. FIG. 5 illustrates a five-week control cavity. Bone regeneration is seen in middle of cavity and in drilling lines. The line between drilled cavity and bone is still seen in most parts of cavity. New bone formation with osteoblasts occurs occasionally in drilling line and also in centre of cavity. FIG. 6 illustrates a five-week clodronate-treated cavity. Cavity is completely filled with new bone and drilling line is still visible but there is a fusion between donor cavity and cortical bone. FIGS. 7 and 8 represent greater magnifications of FIG. 6. In FIG. 7 solid new bone and osteoblasts can be observed. FIG. 8 shows that cortical and new bone are almost completely fused.

Transplants

Figure 9:
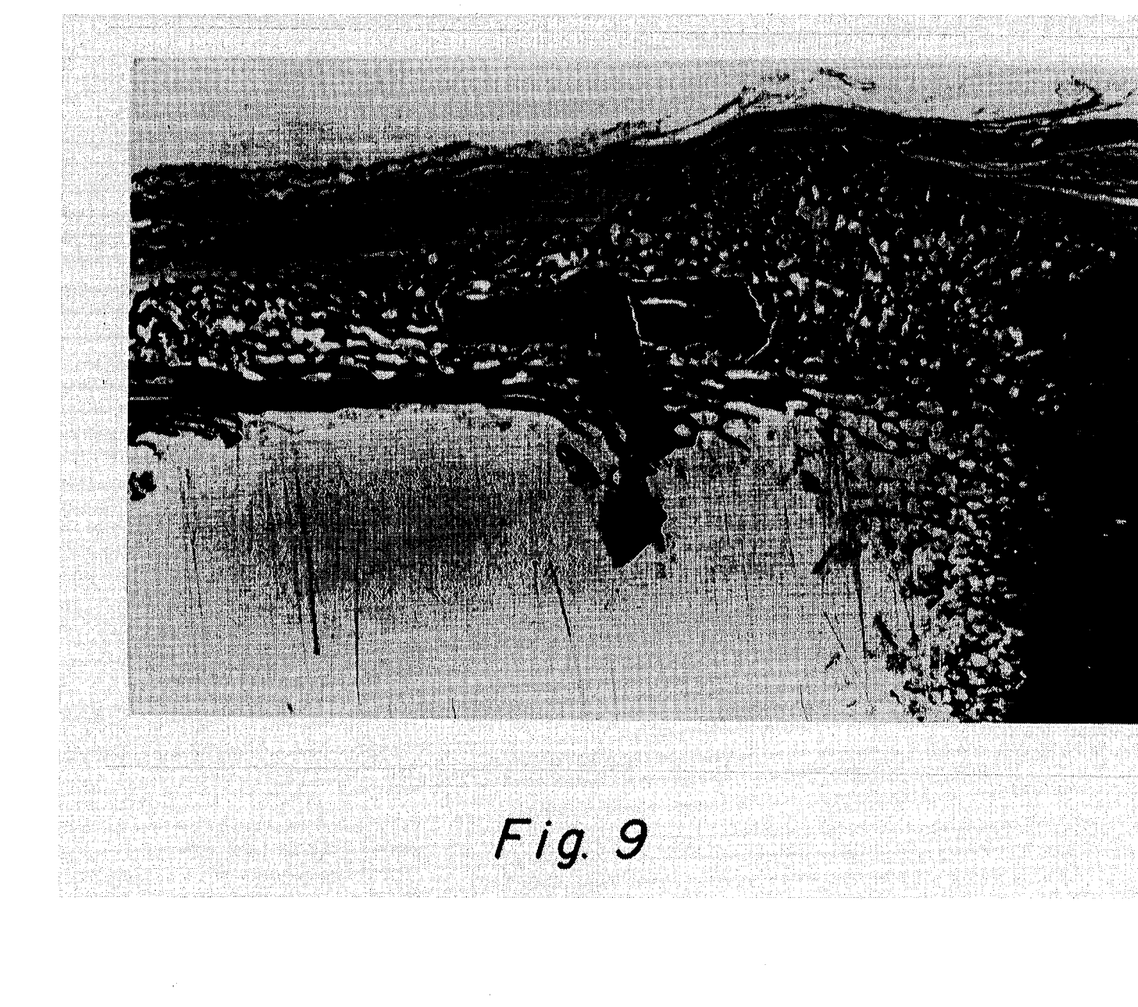
FIG. 9 is a side-view of a four-week clodronate-treated rabbit tibia showing the bone transplant as described in Experiment (I).

The soft tissue and periosteum above the transplants contained more collagen in the clodronate-treated group than in the control animals at all stages. Fourteen-day control specimens exhibited necrotic bone with invading collagen. Treated transplants were beginning to be resorbed at their outer edges. FIG. 9 represents a side-view of four-week clodronate-treated rabbit's tibia. New bone covers transplant. Periosteum is intact but thinner than that above non-operated area. Implant and transplant are in the middle of this specimen. Donor cavity is to the right from transplant and is the reason for new bone formation in normally empty rabbit's spongious bone.

Figure 10:
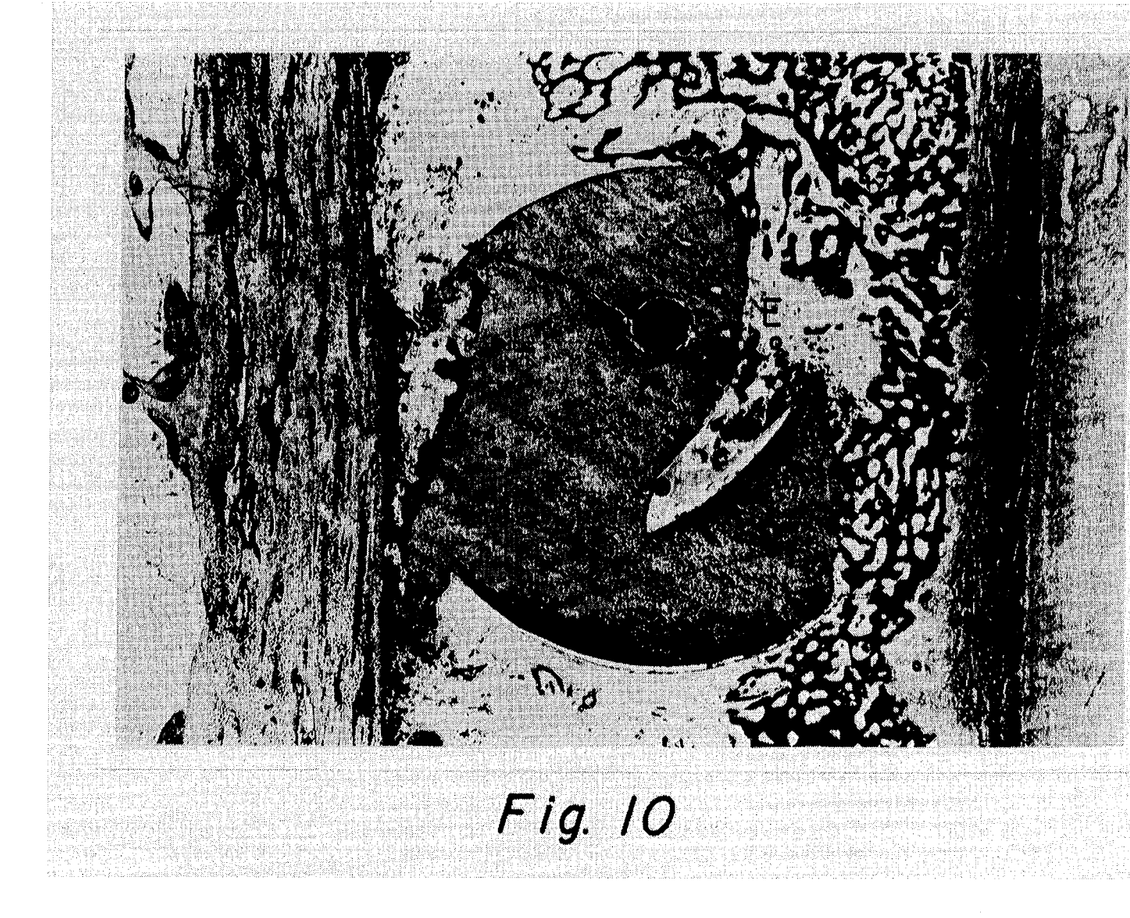
FIG. 10 shows a 21-day clodronate-treated rabbit tibia showing the bone transplant as described in Experiment (I).

Twenty-one-day transplants were partly resorbed. New bone in the resorbed areas was seen in the treated tibiae. No bone formation was seen in control transplants. Bone formation around the implant in the cortical bone area was solid in the clodronate-treated group. FIG. 10 represents a clodronate-treated 21-day specimen. Transplant is partly resorbed and replaced with new bone. The letters A and T represent implant and transplant, respectively, as in FIG. 1, and E represents new bone adjacent to transplant and cortical tibia.

In 35-day specimens there was new bone formation almost throughout the transplants in the treated tibiae. Only solid bone was seen in the control transplants.

Discussion

Regeneration of transplants occurs through microvascularization of the transplant. In a rat embryo study, Ray (Ray R. D., Clin Orthop 1977; 87: 43–48) showed that vascularization of a rat embryo takes 3 to 4 weeks. In a review article, Burchardt (Burchardt H., Clin Orthop 1983; 174: 28–42) states that cancellous bone differs from cortical grafts as far as rates of revascularization are concerned. He suggested that revascularization of cancellous grafts can occur within hours as a result of end-to-end anastomoses from host vessels. Revascularization may be completed within two weeks (Ray R. D.; reference as above). A cortical graft is not penetrated by blood vessels until the sixth day (Ray R. D.; reference as above). Twenty-one days was selected on the basis of the results of a report by Eppley and co-workers (Eppley B. et al., J Oral Maxifollfac Surg 1988; 46: 391–98) as bone regeneration time after implantation. They found that the vascularization of bone grafts in rabbits reached a maximum after 21 days.

The results of the present study confirm the results of earlier reports (Bonjour J. P.; Ray R. D.; both references given above) as far as the control group is concerned. In the medicated rabbits vascularization occurred more quickly than in the control group. The histological findings show clearly that clodronate-treatment makes better bone. The results of the study suggests that bisphosphonates, particularly clodronate, are useful in implant and bone transplant patients where there is a high risk of failure of bone regeneration.

II. Human Tests

Material and methods

The material of this study were 20 edentulous patients. They all came to the Institute of Dentistry, University of Turku, for an implantation procedure. The Institutional Review Board of the Faculty of Medicine at the University of Turku received the project in order to determine whether human subjects are placed at risk. The unanimous decision made by the Institutional Review Board was that the human subjects concerned in this activity would not be placed at any risk. Patients gave permission for an explantation of an extra implant. 10 patients got a daily dose of 1600 mg clodronate disodium until the extra implant was removed (the medicated group) and 10 patients got placebo. The medication and placebo administration, respectively, started one week before the surgery and continued for three weeks after the surgery.

Surgical technique

Figure 11:
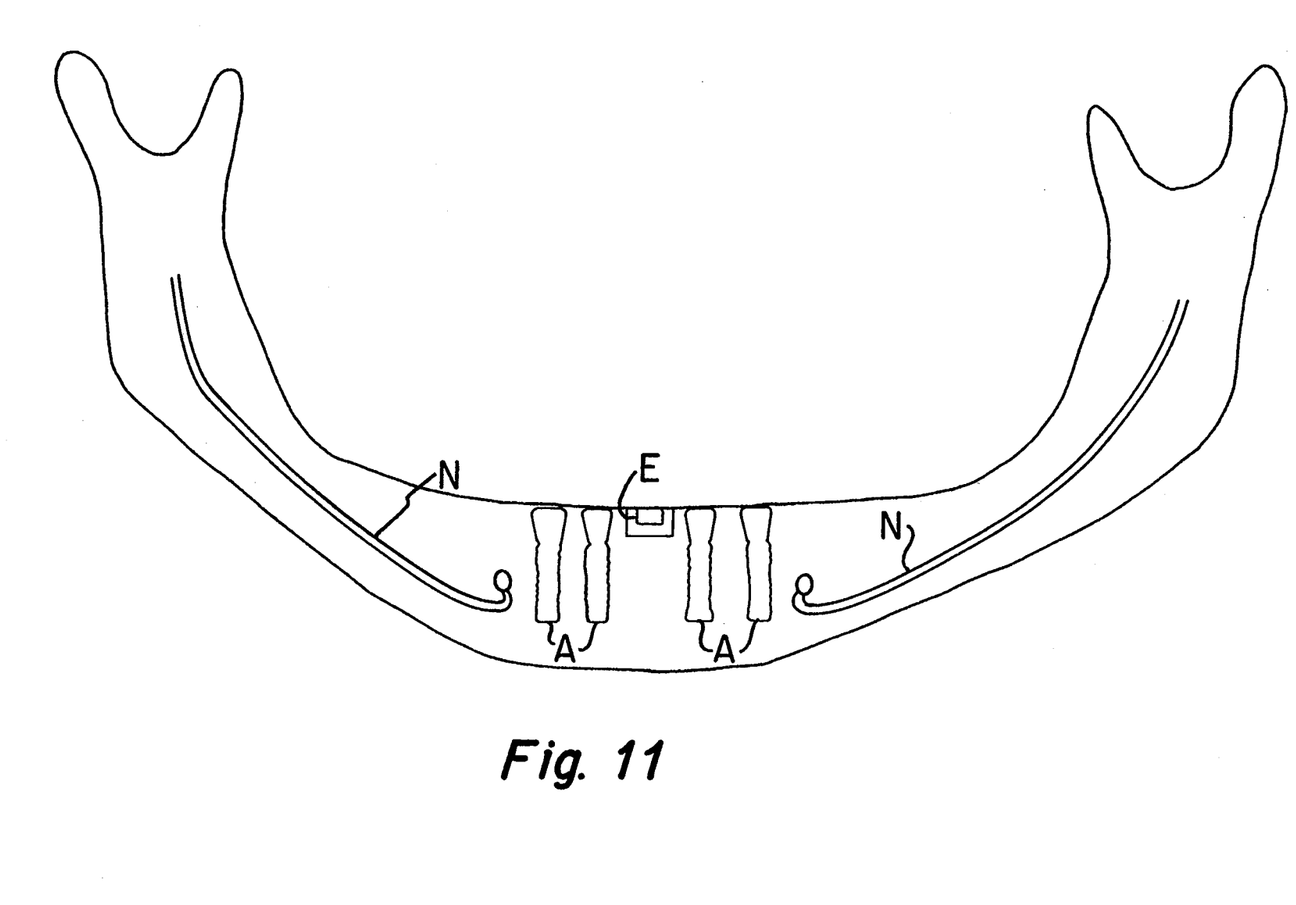
FIG. 11 is a drawing illustrating a front view human mandible with four Astra implants as described in Experiment (II).

Routine method with five Astra implants was used. FIG. 11 is a front view human mandible with four Astra implants, where A means implants, E explanted implant with bone and N is the mandibular nerve. To avoid disturbances in neural function implants are usually placed between the ends of mandibular nerve. At the operation an extra 4 mm screw was installed in the midline of the mandible.

Bone remodelling

At a separate operation the 4 mm extra implant was removed with a trephan bore after 4 (10 patients, equally from both groups) and 12 weeks (10 patients, equally from both groups). The specimens were imbedded in acrylic blocks and divided in midline in two pieces. To the one piece a histological examination was performed. The other one was taken to a SEM-electromicroscopic examination. Electromicroscopic examination in bone-implant interspace and bone in three points with SEM/EDXA (energy dispersive X-ray analysis) was made. At the four different places, two in the upper cortical bone, one in the middle of the implant and one in the bottom of that the following values are calculated: sodium, calcium, phosphor, magnesium and titan. Calcium/phosphor and calcium/magnesium ratio were calculated in 12 points.

Results

Clinical treatment

All the wounds healed well. Two patients had problems with their lower denture under the healing period. They were treated by taking away a part denture. No side-effects were recorded. One patient had pain in his hip orthopedic prosthesis. Those disappeared after clodronate medication.

Histological examinations

One month-specimens

Figure 12:
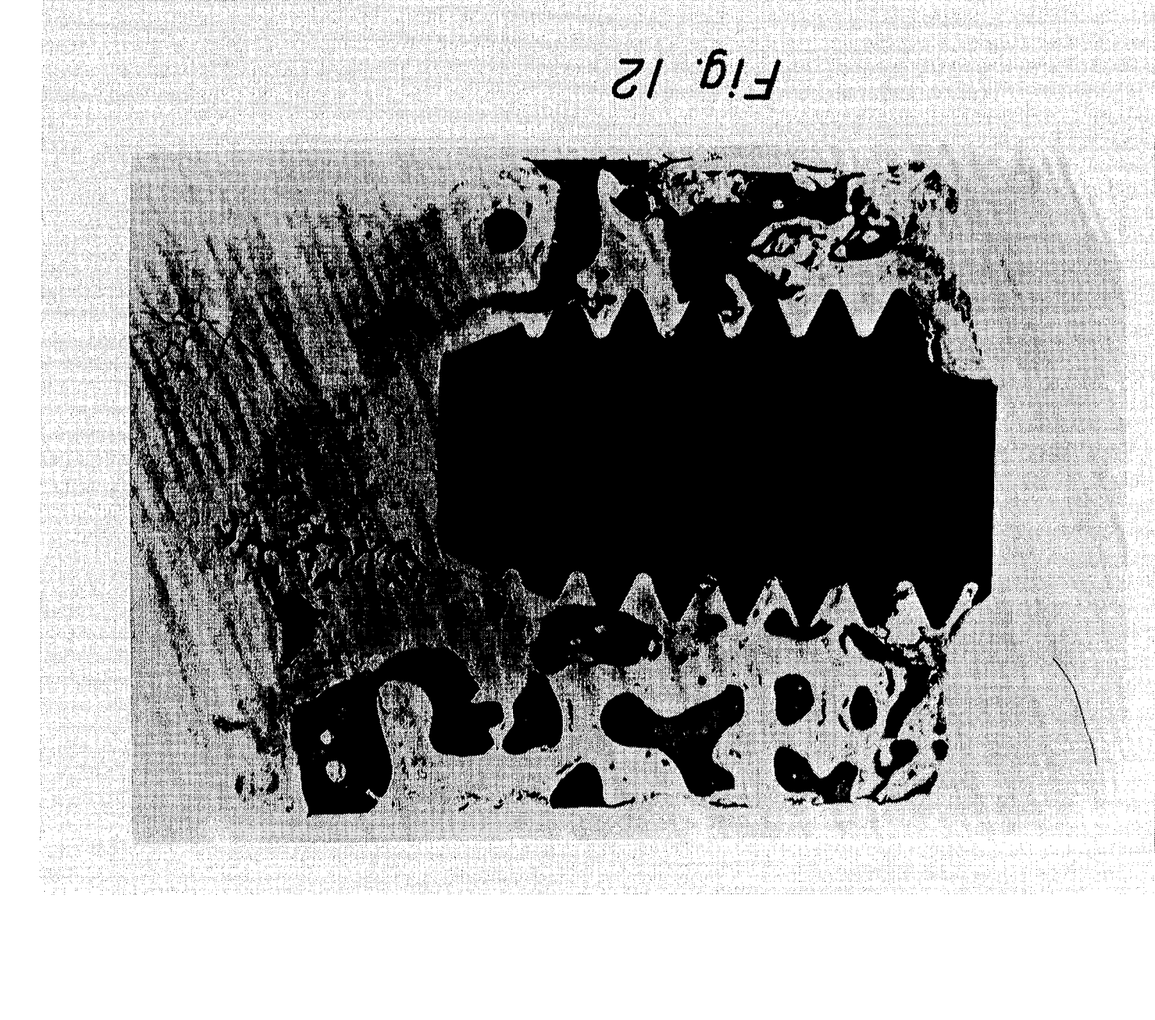
FIG. 12 is a photomicrograph of the bone implant marked with E in FIG. 11.
Figure 13:
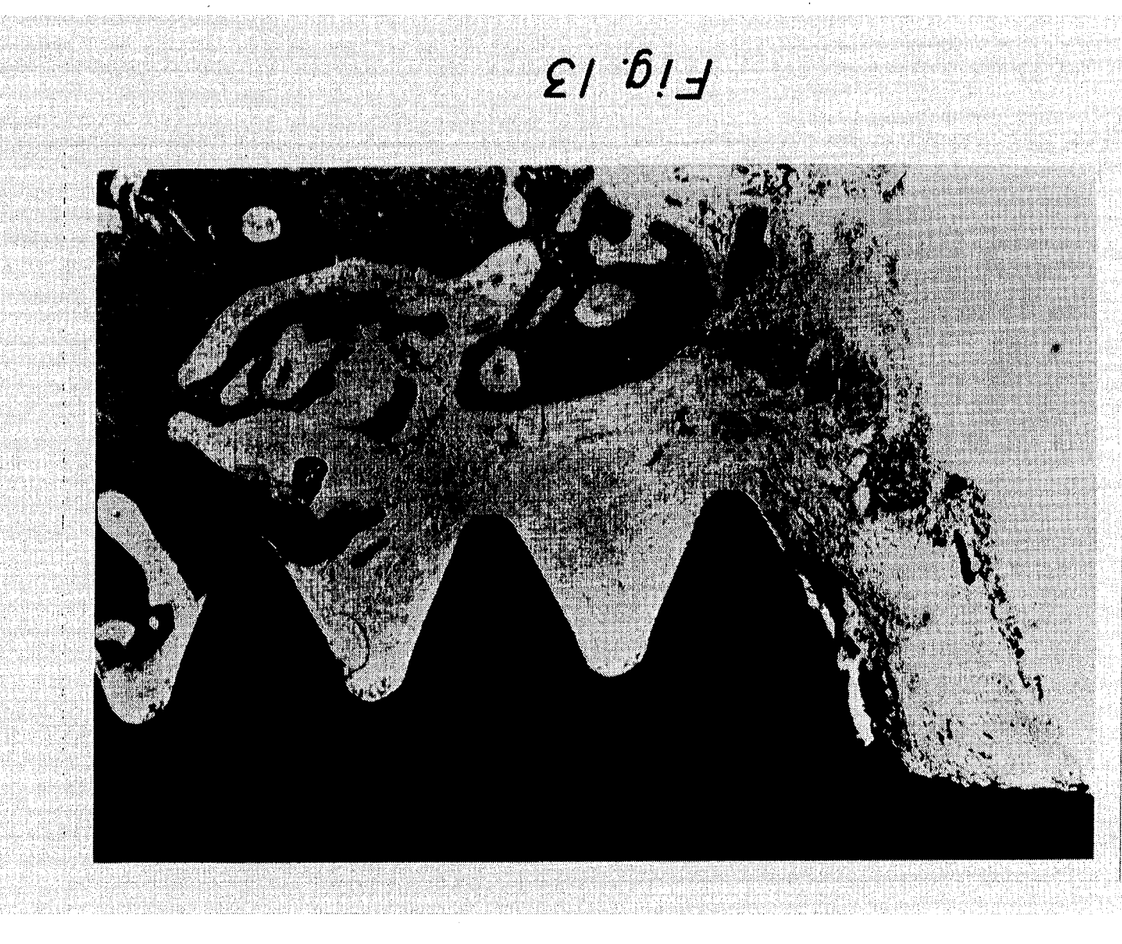
FIG. 13 is a photomicrograph of the bone implant marked with E in FIG. 11 taken at a greater magnification than FIG. 12.

Because all the mandibles were considerably resorbed and when the length of the explanted implant was 4 mm biopsied bone was cortical in all specimens. The histological results are shown in FIGS. 12 and 13, which both disclose the bone-implant specimen marked with E in FIG. 11. FIG. 13 represents a greater magnification of FIG. 12. No spongious bone was seen. Soft gingival tissue covering the implants was healthy.

Histological examination revealed no more new bone in medicated than control-mandibles. There were no signs of inflammation. The space between implant and bone was mainly filled with collagen. In same points the contact between bone and implant was close. This is natural, because screwed Astra implants were used.

SEM-results

Figure 14:
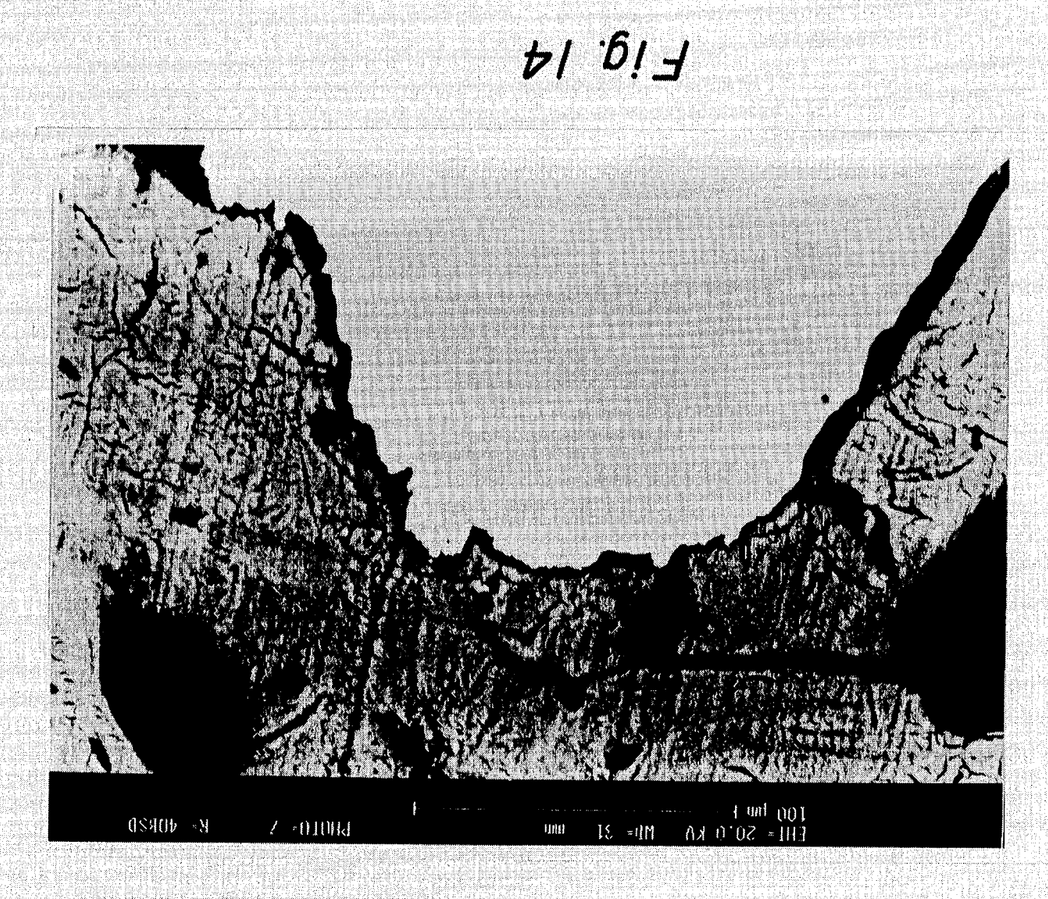
FIG. 14 is a photomicrograph of a human mandible 4 weeks after implantation of an extra-ester implant where numbers 1 to 5 indicate the points where mineral concentrations were measured as reported in Table III.

Table III shows the SEM results in human mandibles 4 weeks after implantation of an extra Astra implant. The 10 000×SEM figure is the same as that in FIGS. 11 and 12. The exact points where mineral concentrationas are measured are shown with small numbers in FIG. 14. The mean values of those standard points are given in Table III.

TABLE III

|  | CaO | $P_2O_5$ | CaO/$P_2O_5$ | Mg | Na |
|---|---|---|---|---|---|
| control | 56 | 30 | 1.8 | 1.2 | 8.2 |
| medicated | 72 | 40 | 1.8 | 0.9 | 2.8 |

The values are given in weight percent.

Discussion

Histological and SEM-pictures were similar in both groups. No differences under light and SEM-cross-over pictures were seen. In one-month specimens $P_2O_5$ and CaO are both significantly greater in the medicated than in control mandibles. This means that rapid bone formation had begun, osteoclasts have resorbed bone. Osteogenesis is more intensive in medicated than in control patients.

We claim:

1. A method of enhancing the formation of bone tissue and/or eliminating late complications subsequent to bone surgery in connection with endo-osteal implantation comprising administering an amount, which is safe and sufficient to promote the formation of bone tissue and/or eliminate late complications, of a compound of the formula wherein X is H, OH, Cl, F or a methyl group and Y is Cl, OH, —(CH$_2$)$_2$—N(CH$_3$)—(CH$_2$)$_4$—CH$_3$, —(CH$_2$)$_n$—CH$_3$ or —(CH$_2$)$_n$—NH$_2$, where n is zero or an integer of 1 to 8, —NHZ, where Z is pyridinyl or cycloheptyl, —SZ′, where Z′ is pyridinyl or chloro-substituted phenyl, or Y is a pyridinylsubstituted lower alkyl chain; or a non-toxic, pharmaceutically acceptable salt or ester thereof to a bone surgery patient during a period of 1 to 3 weeks before said surgery and/or after said surgery for a period of 1 to 6 months.

2. The method according to claim 1 wherein the compound administered is selected from the group consisting of clodronate, pamidronate, etidronate, alendronic acid, neridronic acid, risedronic acid, tiludronate, (cycloheptylamino)methylenebisphosphonic acid, 1-hydroxy-3-(methylpentylamino)-propylidenebisphosphonic acid and pharmaceutically acceptable salts and esters of said compounds.

3. The method according to claim 2 wherein the compound administered is clodronate or its pharmaceutically acceptable salt or ester.

4. The method according to claim 3 wherein the compound administered is clodronate disodium.

5. The method according to claim 1 which comprises administering an amount, which is safe and sufficient to promote the formation of bone tissue, of a compound of formula (I) or a non-toxic, pharmaceutically acceptable salt or ester thereof to a transplantation surgery patient.

6. The method according to claim 1 which comprises administering an amount, which is safe and sufficient to promote the formation of bone tissue, of a compound of formula (I) or a non-toxic, pharmaceutically acceptable salt or ester thereof to an endo-osteal prosthesis surgery patient.

7. The method according to claim 6 which comprises administering an amount, which is safe and sufficient to promote the formation of bone tissue, of a compound of formula (I) or a non-toxic, pharmaceutically acceptable salt or ester thereof to an implantation surgery patient.

8. The method according to claim 7 which comprises administering an amount, which is safe and sufficient to promote the formation of bone tissue, of a compound of formula (I) or a non-toxic, pharmaceutically acceptable salt or ester thereof to a dental implantation surgery patient.

9. The method according to claim 8 wherein the compound administered is selected from the group consisting of clodronate, pamidronate, etidronate, alendronic acid, neridronic acid, risedronic acid, tiludronate, (cycloheptylamino)methylenebisphosphonic acid, 1-hydroxy-3-(methylpentylamino)-propylidenebisphosphonic acid and pharmaceutically acceptable salts and esters of said compounds.

10. The method according to claim 9 wherein the compound administered is clodronate or its pharmaceutically acceptable salt or ester.

11. The method according to claim 10 wherein the compound administered is clodronate disodium.

* * * * *